(12) United States Patent
Yoon et al.

(10) Patent No.: US 10,722,202 B2
(45) Date of Patent: Jul. 28, 2020

(54) X-RAY APPARATUS FOR REAL-TIME THREE-DIMENSIONAL VIEW

(71) Applicant: SEOUL NATIONAL UNIVERSITY HOSPITAL, Seoul (KR)

(72) Inventors: Chang Hwan Yoon, Seoul (KR); Dong Hoon Han, Seoul (KR)

(73) Assignee: Seoul National University Hospital, Seoul (KR)

( * ) Notice: Subject to any disclaimer, the term of this patent is extended or adjusted under 35 U.S.C. 154(b) by 18 days.

(21) Appl. No.: 16/095,905

(22) PCT Filed: Apr. 26, 2017

(86) PCT No.: PCT/KR2017/004440
§ 371 (c)(1),
(2) Date: Oct. 23, 2018

(87) PCT Pub. No.: WO2017/188726
PCT Pub. Date: Nov. 2, 2017

(65) Prior Publication Data
US 2019/0261937 A1 Aug. 29, 2019

(30) Foreign Application Priority Data
Apr. 26, 2016 (KR) ......................... 10-2016-0051074

(51) Int. Cl.
*A61B 6/00* (2006.01)
*A61B 6/02* (2006.01)
(Continued)

(52) U.S. Cl.
CPC ................ *A61B 6/487* (2013.01); *A61B 6/00* (2013.01); *A61B 6/02* (2013.01); *A61B 6/022* (2013.01);
(Continued)

(58) Field of Classification Search
CPC .. A61B 6/487; A61B 6/00; A61B 6/10; A61B 6/02; A61B 6/022; A61B 6/0407;
(Continued)

(56) References Cited

U.S. PATENT DOCUMENTS 9,579,071 B2 * 2/2017 Lee ...................... A61B 6/022
2008/0089472 A1 4/2008 Yoon
(Continued)

FOREIGN PATENT DOCUMENTS

JP 2005-261 A 1/2005
JP 2009133837 A 6/2009
(Continued)

*Primary Examiner* — Christine S. Kim
(74) *Attorney, Agent, or Firm* — Husch Blackwell LLP

(57) ABSTRACT

The present invention comprises: a first X-ray irradiation apparatus and a second X-ray irradiation apparatus for irradiating a subject with X-rays; an X-ray generation unit supporting so that first and second X-rays irradiated onto the subject are detected by a set detector when the subject is irradiated with the first and second X-rays from the first and second X-ray irradiation apparatuses, respectively; and a mode selection unit for allowing selection of any one mode from among a 2D imaging mode and 3D imaging mode, wherein the angles with respect to the subject of the first and second X-ray irradiation apparatuses are determined on the basis of said any one mode selected by means of the mode selection unit from among the 2D imaging mode and 3D imaging mode. According to the present invention, the mode can be easily selected according to need from among the 2D imaging mode and 3D imaging mode.

9 Claims, 3 Drawing Sheets

(51) Int. Cl.
  *A61B 6/04* (2006.01)
  *A61B 6/06* (2006.01)
  *A61B 6/10* (2006.01)

(52) U.S. Cl.
  CPC .............. *A61B 6/0407* (2013.01); *A61B 6/06* (2013.01); *A61B 6/10* (2013.01); *A61B 6/107* (2013.01); *A61B 6/4007* (2013.01); *A61B 6/4208* (2013.01); *A61B 6/466* (2013.01); *A61B 6/582* (2013.01); *A61B 6/4441* (2013.01)

(58) Field of Classification Search
  CPC ......... A61B 6/06; A61B 6/107; A61B 6/4007; A61B 6/4208; A61B 6/466; A61B 6/582; A61B 6/4441; A61B 6/54; A61B 6/4429; A61B 6/5223
  See application file for complete search history.

(56) References Cited

U.S. PATENT DOCUMENTS

| | | | |
|---|---|---|---|
| 2008/0095308 A1* | 4/2008 | Kano | A61B 6/022 378/41 |
| 2008/0095423 A1* | 4/2008 | Redel | A61B 6/481 382/131 |
| 2010/0040196 A1* | 2/2010 | Zhang | A61B 6/022 378/42 |
| 2014/0112430 A1* | 4/2014 | Lee | A61B 6/022 378/4 |
| 2016/0310088 A1 | 10/2016 | Kim et al. | |

FOREIGN PATENT DOCUMENTS

| | | |
|---|---|---|
| JP | 2011130922 A | 7/2011 |
| JP | 2013233258 A | 11/2013 |
| JP | 2014-57797 A | 4/2014 |
| KR | 10-2008-0030745 A | 4/2008 |
| KR | 10-2008-0055081 A | 6/2008 |
| KR | 10-2015-0073419 A | 7/2015 |
| KR | 10-2016-0006382 A | 1/2016 |
| WO | 2015050016 A1 | 4/2015 |

\* cited by examiner

X-RAY APPARATUS FOR REAL-TIME THREE-DIMENSIONAL VIEW

FIELD OF THE INVENTION

The present invention relates to a real-time X-ray fluoroscopic device; and more particularly, to the real-time X-ray fluoroscopic device, including: an X-ray generator, which includes a first and a second X-ray irradiators, if a first X-ray and a second X-ray irradiated respectively from the first and the second X-ray irradiators pass through a subject, supporting the first X-ray and the second X-ray to be detected by a detector; and a mode selector capable of selecting either of a 2D imaging mode and a 3D imaging mode; wherein an angle of the first X-ray irradiator to the subject and that of the second X-ray irradiator to the subject are determined by referring to information on either of the 2D imaging mode and the 3D imaging mode selected by the mode selector; and wherein information on the first X-ray and the second X-ray detected by the detector is provided to an image processing unit to allow imaging of the detected first X-ray and the detected second X-ray to be processed.

BACKGROUND OF THE INVENTION

In a conventional angiographic unit, an image intensifier receives an X-ray signal if an X-ray is irradiated onto a human body, and transmits the received the X-ray signal to a camera tube, by which the X-ray signal is converted into an image signal. When the image signal is reconfigured by several image-processing circuits and sent to a monitor, an operator performs treatments while watching the monitor. As such, since there are few techniques for reconstructing 3D images in a real-time fluoroscopic field, it is difficult for the operator to recognize accurate pathways, directions, etc. of blood vessels with 2D images upon a treatment.

Upon taking an image of blood vessels by using an angiographic unit, a performance of the angiographic unit is evaluated by a resolving power, which is determined by contrast resolution, time resolution, and spatial resolution. The contrast resolution is an ability of discerning differences between light and darkness of a substance and the time resolution is an ability of discerning a minimum time interval regarding an input signal. The spatial resolution, which is the most important element in determining the resolving power, is an ability to geometrically separate and discern an adjacent substance, but the reconstruction of three-dimension (3D) as an element for improving the spatial resolution is scarcely considered.

To overcome such problems, a method for obtaining 2D images orthogonal with each other by using two C-arms and then reconstructing a 3D structure has been suggested. However, the method has also problems of causing a double radiation exposure due to two X-ray generators and two detectors, and failing to obtain images from various angles.

SUMMARY OF THE INVENTION

It is an object of the present invention to solve all the aforementioned problems.

It is another object of the present invention to visualize blood vessels in 3D as real by accurately expressing locations of overlapped structures for blood vessels, and thereby supporting an operator to recognize locations of lesions and accessible directions upon a treatment.

It is still another object of the present invention to allow an operator to select conveniently either a 2D imaging mode or a 3D imaging mode depending on a purpose of use.

In accordance with one aspect of the present invention, there is provided a real-time X-ray fluoroscopic device, including: an X-ray generator, which includes a first and a second X-ray irradiators, if a first X-ray and a second X-ray irradiated respectively from the first and the second X-ray irradiators pass through a subject, supporting the first X-ray and the second X-ray to be detected by a detector; and a mode selector capable of selecting either of a 2D imaging mode and a 3D imaging mode; wherein an angle of the first X-ray irradiator to the subject and that of the second X-ray irradiator to the subject are determined by referring to information on either of the 2D imaging mode and the 3D imaging mode selected by the mode selector; and wherein information on the first X-ray and the second X-ray detected by the detector is provided to an image processing unit to allow imaging of the detected first X-ray and the detected second X-ray to be processed.

In addition, recordable media that are readable by a computer for storing a computer program to execute the method of the present invention is further provided.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Figure 1:
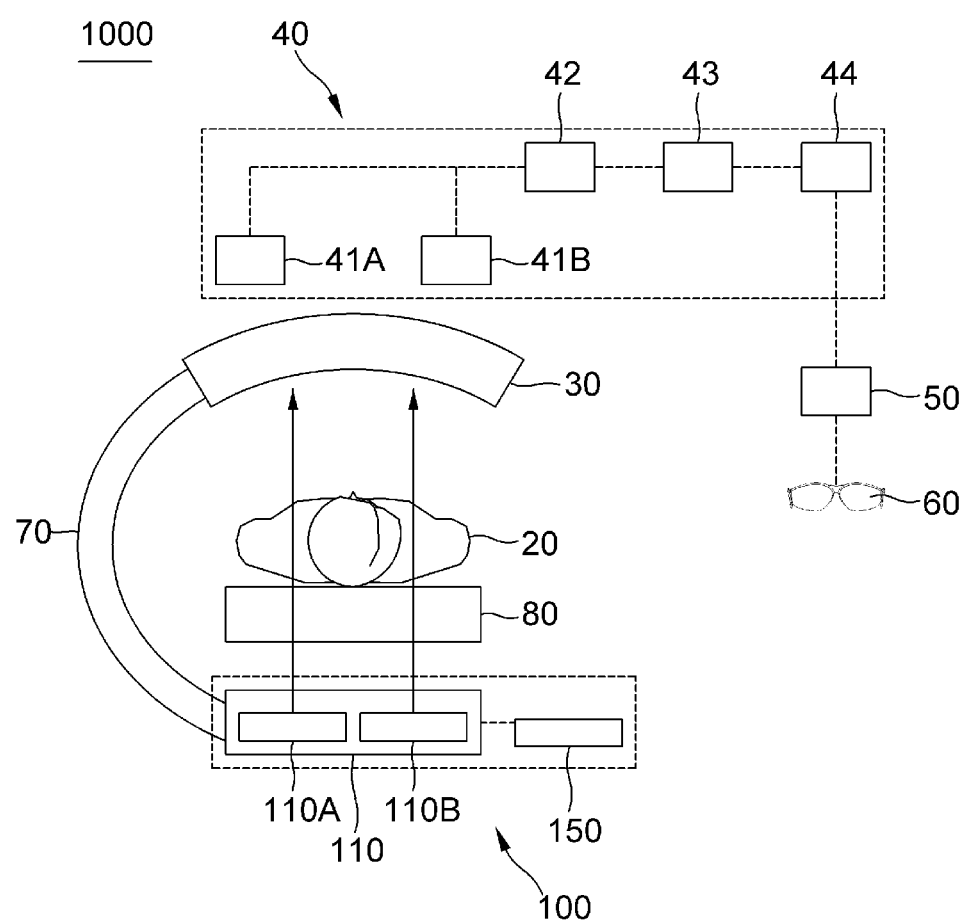
FIG. 1 is a diagram of a whole system which includes a real-time X-ray fluoroscopic device in accordance with one example embodiment of the present invention.

Detailed explanations of the present invention explained below refer to attached drawings that illustrate specific embodiment examples of this present that may be executed. These embodiments are described in sufficient detail to enable those skilled in the art to practice the invention. It is to be understood that the various embodiments of the present invention, although different, are not necessarily mutually exclusive. For example, a particular feature, structure, or characteristic described herein in connection with one embodiment may be implemented within other embodiments without departing from the spirit and scope of the present invention. In addition, it is to be understood that the position or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

To make those skilled in the art embody the present invention easily, desirable example embodiments of the present invention will be explained more specifically by referring to drawings attached.

First of all, FIG. 1 illustrates a diagram of a whole system 1000 which includes a real-time X-ray fluoroscopic device 100 in accordance with one example embodiment of the present invention.

By referring to FIG. 1, the whole system 1000 in accordance with the present invention may include the X-ray fluoroscopic device 100, a detector 30, an image-processing unit 40, a monitor 50, 3D goggles 60, a C-arm 70, and a table 80, etc.

Furthermore, the X-ray fluoroscopic device 100 may include an X-ray generator 110 and a mode selector 150. More specifically, the X-ray generator 110 may include a first X-ray irradiator 110A and a second X-ray irradiator 110B for irradiating X-rays respectively onto a subject 20 and the mode selector 150 may perform a function of selecting either of a 2D imaging mode and a 3D imaging mode. The function of the mode selector 150 will be explained later by referring to FIG. 2 and FIG. 3.

For reference, the real-time X-ray fluoroscopic device 100 may be configured to include at least some of the detector 30, the image-processing unit 40, which may also be called as an image-processing device, an image-processing terminal, an image-controlling server, etc., the monitor 50, the 3D goggles 60, the C-arm 70, and the table 80, but they may not be essential components as the case may be. In this specification, the real-time X-ray fluoroscopic device 100 may be configured with the X-ray generator 110 and the mode selector 150 as essential components.

Herein, the X-ray generator 110 of the present invention may be configured with a first X-ray tube 111A formed in the first X-ray irradiator 110A and a second X-ray tube 111B formed in the second X-ray irradiator 110B, and these will be explained later by referring to FIG. 2 and FIG. 3.

Next, if the first X-ray and the second X-ray irradiated respectively from the first X-ray irradiator 110A and the second X-ray irradiator 110B pass through the subject 20, the detector 30 may perform a function of detecting the first X-ray and the second X-ray. For example, the detector 30 may be curved.

Meanwhile, the detector 30 may receive the first X-ray and the second X-ray generated respectively from the first X-ray tube 111A and the second X-ray tube 111B alternately. For example, if the first X-ray is received as a source for generating right-side images with 15 fps and the second X-ray is received as a source for generating left-side images with 15 fps, the detector 30 combines them to thereby provide the combined images, i.e., images of stereovision for both eyes with 15 fps, to an operator.

Next, the image-processing unit 40 may include a first TV camera 41A and a second TV camera 41B for respectively taking the first x-ray and the second X-ray detected by the detector 30, a TV projector 42 for projecting images taken by the first TV camera 41A and the second TV camera 41B, an image controller 43 for recombining and calibrating the images projected by the TV projector 42, and a digital imaging unit 44 for converting the images recombined by the image controller 43 into digital and analogue signals.

Meanwhile, the image-processing unit 40 may allow the converted signals to be outputted and be observed in a form of 2D images or 3D images through the monitor 50 and may allow the operator to perceive the 3D images through the 3D goggles 60. Herein, the 3D goggles 60 may be implemented in variety of forms. For example, it may provide a 3D effect by polarizing its right lens and left lens differently. Further, the 3D goggles 60 may also include a module for shielding X-rays to prevent eyes from being damaged.

Accordingly, the present invention may allow a one images to be perceived through the left eye and allow the other images to be perceived through the right eye in order to visualize blood vessels in 3D as real and therefore, it may support the operator to recognize locations of lesions and accessible directions upon a treatment by accurately expressing locations of overlapped blood vessel structures.

Explanation on a function of the mode selector 150 will be made below by referring to FIGS. 2 and 3.

For reference, the mode selector 150 performs a function of allowing a doctor to select either of the 2D imaging mode and the 3D imaging mode. The doctor may utilize a simple hardware to be used for communicating with the mode selector 150 which also include a communication module. In some cases, a user interface may be provided to the doctor's mobile terminal for allowing the doctor to simply select a mode.

Figure 2:
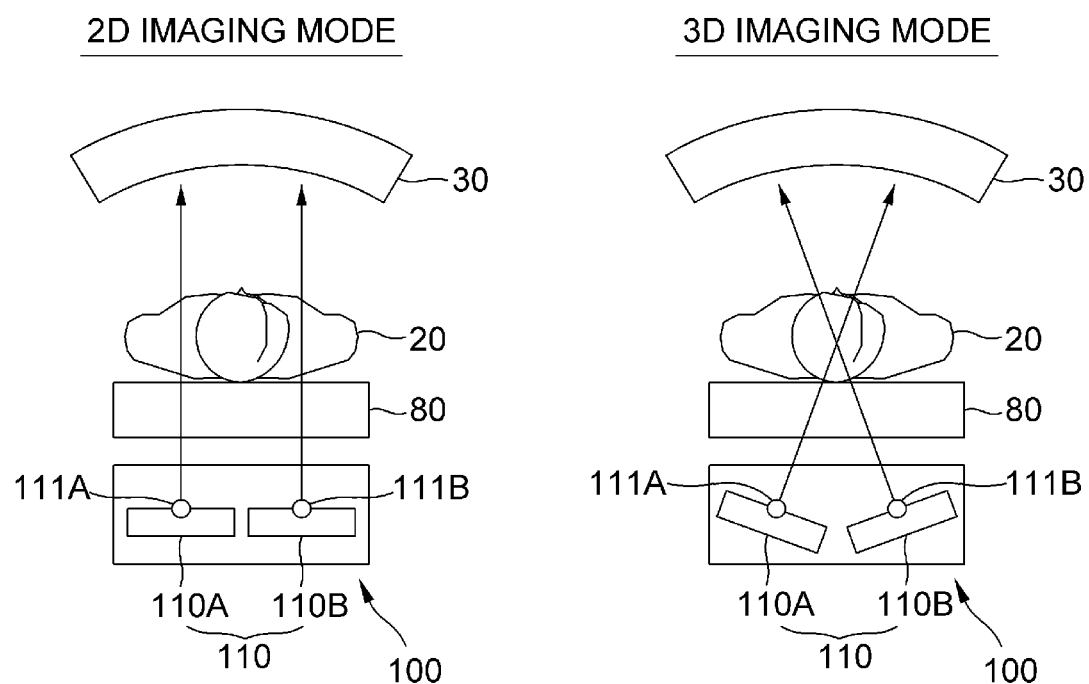
FIG. 2 is an exemplary diagram to explain a 2D imaging mode and a 3D imaging mode of the real-time X-ray fluoroscopic device in accordance with one example embodiment of the present invention.

FIG. 2 is an exemplary diagram to explain the 2D imaging mode and the 3D imaging mode of the real-time X-ray fluoroscopic device 100 in accordance with one example embodiment of the present invention.

By referring to FIG. 2, more specifically, an angle of the first X-ray tube 111A and that of the second X-ray tube 111B are controlled to allow X-ray beams to be pass through the subject in a line in the 2D imaging mode, and the angle of the first X-ray tube 111A and that of the second X-ray tube 111B are controlled to allow the respective X-ray beams to be intersected at the subject in the 3D imaging mode.

In addition, a distance between the first X-ray tube 111A and the second X-ray tube 111B in the 2D imaging mode may be properly adjusted in consideration of resolution of the 2D images, etc. and X-rays outputted from the first X-ray tube 111A and the second X-ray tube 111B may be provided alternately to reduce radiation exposure.

In FIG. 2, it is illustrated that the first X-ray tube 111A and the second X-ray tube 111B is slightly apart from each other, but a structure of the first X-ray tube 111A and the second X-ray tube 111B being in contact with each other may also be possible as the case may be. In this case, individual X-ray beams outputted through the first X-ray tube 111A and the second X-ray tube 111B being in contact with each other may be provided like one large X-ray beam.

Meanwhile, the first X-ray irradiator 110A and the second X-ray irradiator 110B may be adjusted to be slightly tilted for the 3D imaging mode. For example, a tilt angle may be about 3 to 6 degrees.

Figure 3:
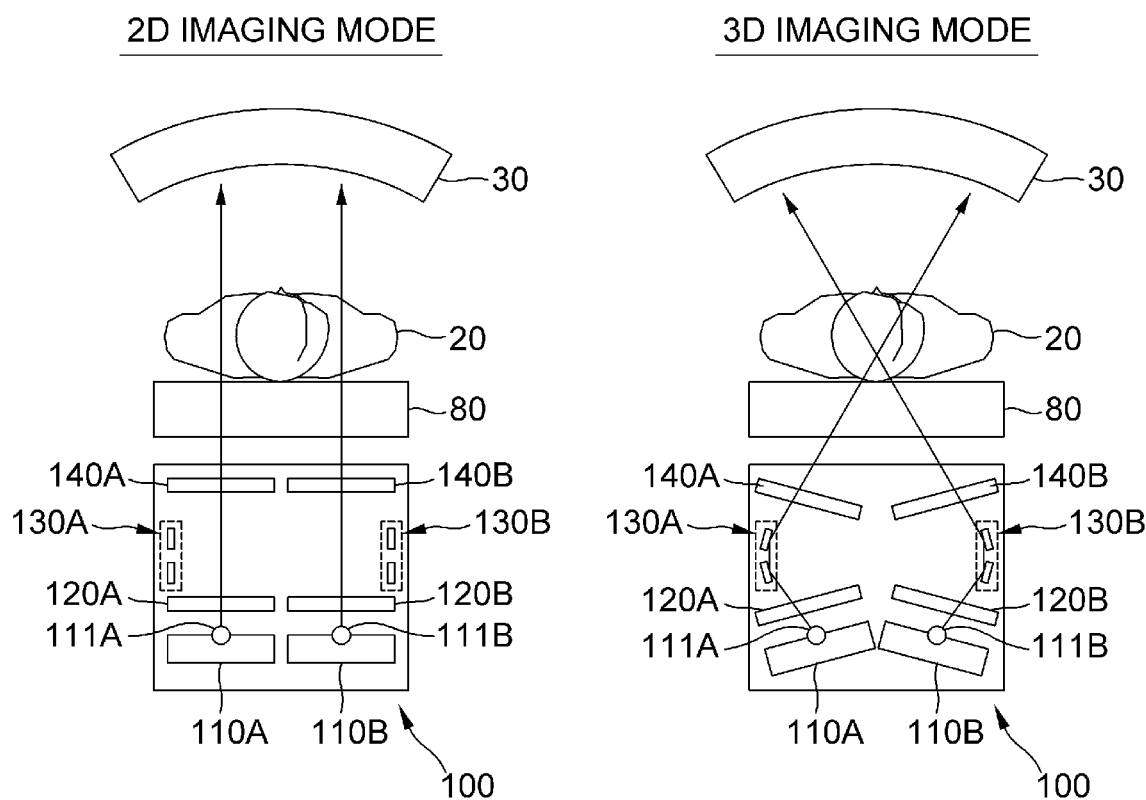
FIG. 3 is an exemplary diagram to explain the 2D imaging mode and the 3D imaging mode of the real-time X-ray fluoroscopic device in accordance with another example embodiment of the present invention.

Next, FIG. 3 is an exemplary diagram to explain the 2D imaging mode and the 3D imaging mode of the real-time X-ray fluoroscopic device 100 in accordance with another example embodiment of the present invention.

By referring to FIG. 3, the real-time X-ray fluoroscopic device 100 in accordance with another example embodiment of the present invention may include the X-ray generator 110, a first lower collimator 120A, a second lower collimator 120B, a first reflection unit 130A, a second reflection unit 130B, a first upper collimator 140A, and a second upper collimator 140B.

More specifically, the X-ray generator 110 may include the first X-ray tube 111A and the second X-ray tube 111B and may output X-rays respectively from the first X-ray tube 111A and the second X-ray tube 111B. Herein, angles of X-rays from the first X-ray tube 111A and the second X-ray tube 111B may be controlled by a mode selector which is not illustrated.

Next, the first lower collimator 120A may perform a function of relaying the X-ray outputted from the first X-ray tube 111A and the second lower collimator 120B may perform a function of relaying the X-ray outputted from the second X-ray tube 111B. Herein, angles of the first lower collimator 120A and the second lower collimator 120B may also be controlled by the mode selector 150, which is not illustrated, corresponding to angles of X-rays outputted from the first X-ray tube 111A and the second X-ray tube 111B.

Further, the first reflection unit 130A and the second reflection unit 130B may include one or more small reflecting plates respectively, and angles of the first reflection unit 130A and the second reflection unit 130B may be controlled not to affect optical paths during the 2D imaging mode and to affect them during the 3D imaging mode. Herein, each of the first and the second reflection units 130A and 130B may be at least one mirror used for X-ray optics. Each mirror may be made of glass, ceramic or metal foil and may be coated by a reflective layer. Furthermore, a reflecting material most commonly used for the X-ray optics may be gold or iridium. The specific explanation on this may include a search result with keywords "mirrors for X-ray optics" in Wikipedia.

Next, the first and the second upper collimators 140A and 140B perform functions of transmitting the X-rays relayed from the first and the second lower collimators 120A and 120B toward the subject 20 during the 2D imaging mode, and transmitting the X-rays, having been reflected by the first and the second reflection units 130A and 130B, toward the subject 20 during the 3D imaging mode.

For reference, the first and the second reflection units 130A and 130B may be placed between (i) the first and the second lower collimators 120A and 120E and (ii) the first and the second upper collimators 140A and 140B, respectively, and at the same time may be placed on side walls not to affect optical paths during the 2D imaging mode.

Examples of the operation during the 2D imaging mode and the 3D imaging mode will be more specifically explained below.

During the 2D imaging mode, normal lines of the first tube 111A and the second X-ray tube 111B and normal lines of the first and the second lower collimators 120A and 120B are controlled to be parallel, and angles of the first and the second reflection units 130A and 130B are controlled not to affect optical paths of the individual X-rays outputted from the first X-ray tube 111A and the second X-ray tube 111B. At this time, by controlling normal lines of the first and the second upper collimators 140A and 140B and those of the first and the second lower collimators 120A and 120B to be parallel, the X-rays received from the first and the second lower collimators 120A and 120B may be transmitted to the first and the second upper collimators 140A and 140B and then irradiated onto the subject 20.

Meanwhile, more specifically, during the 3D imaging mode, angles of individual X-rays outputted from the first and the second X-ray tube 111A and 111B and angles of the first and the second lower collimators 120A and 120B are controlled such that the individual X-rays passing therethrough may be transmitted toward the first and the second reflection units 130A and 130B and at the same time angles of the first and the second reflection units 130A and 130B and those of the first and the second upper collimators 140A and 140B may be controlled such that the individual X-rays passing through the first and the second upper collimators 140A and 140B are transmitted toward an area to be treated on the subject 20.

The present invention has an effect of visualizing blood vessels in as real by accurately expressing locations of overlapped structures for blood vessels, thereby supporting the operator to recognize locations of lesions and accessible directions upon a treatment.

Besides, the present invention has another effect of supporting the operator to select conveniently either the 2D imaging mode or the 3D imaging mode depending on a purpose of use.

The embodiments of the present invention as explained above can be implemented in a form of executable program command through a variety of computer means recordable to computer readable media. The computer readable media may include solely or in combination, program commands, data files, and data structures. The program commands recorded to the media may be components specially designed for the present invention or may be usable to a skilled human in a field of computer software. Computer readable media include magnetic media such as hard disk, floppy disk, and magnetic tape, optical media such as CD-ROM and DVD, magneto-optical media such as floptical disk and hardware devices such as ROM, RAM, and flash memory specially designed to store and carry out program commands. Program commands include not only a machine language code made by a complier but also a high level code that can be used by an interpreter etc., which is executed by a computer. The aforementioned hardware device can work as more than a software module to perform the action of the present invention and they can do the same in the opposite case.

As seen above, the present invention has been explained by specific matters such as detailed components, limited embodiments, and drawings. They have been provided only to help more general understanding of the present invention. It, however, will be understood by those skilled in the art that various changes and modification may be made from the description without departing from the spirit and scope of the invention as defined in the following claims.

Accordingly, the thought of the present invention must not be confined to the explained embodiments, and the following patent claims as well as everything including variations equal or equivalent to the patent claims pertain to the category of the thought of the present invention.

What is claimed is:

1. A real-time X-ray fluoroscopic device, comprising:
   an X-ray generator including a first X-ray irradiator and a second X-ray irradiator, wherein the first and the second X-ray irradiators are operable to irradiate, respectively, a first X-ray and a second X-ray for passage through a subject and detection by a detector; and
   a mode selector capable of selecting either of a 2D imaging mode and a 3D imaging mode;
   wherein an angle of the first X-ray irradiator to the subject and an angle of the second X-ray irradiator to the subject are determined by referring to information on either of the 2D imaging mode and the 3D imaging mode selected by the mode selector; and
   wherein information on the first X-ray and the second X-ray detected by the detector is provided to an image processing unit to allow imaging of the detected first X-ray and the detected second X-ray to be processed.

2. The fluoroscopic device of claim 1, wherein a first X-ray tube is formed in the first X-ray irradiator and a second X-ray tube is formed in the second X-ray irradiator; and wherein an angle of the first X-ray tube and an angle of the second X-ray tube are controlled to allow the first X-ray and the second X-ray to pass through the subject in a line in the 2D imaging mode, and the angle of the first X-ray tube and the angle of the second X-ray tube are controlled to allow the first X-ray and the second X-ray to be intersected at the subject in the 3D imaging mode.

3. The fluoroscopic device of claim 1, wherein a first X-ray tube is formed in the first X-ray irradiator and a second X-ray tube is formed in the second X-ray irradiator; and wherein the X-ray generator includes:
a first lower collimator for relaying the first X-ray generated from the first X-ray tube and a second lower collimator for relaying the second X-ray generated from the second X-ray tube,
a first reflection unit and a second reflection unit, wherein the first and the second reflection units respectively include one or more reflecting plates capable of receiving individual X-rays from the first and the second lower collimators and reflecting the individual X-rays with a certain angle of reflection, and
a first upper collimator and a second upper collimator for relaying the individual X-rays received from the first and the second reflection units to the subject,
wherein normal lines of the first and the second X-ray tubes, normal lines of the first and the second lower collimators and normal lines of the first and the second upper collimators are controlled to be parallel and at the same time the first and the second reflection units are controlled not to affect optical paths of the individual X-rays of the first and the second X-ray tubes during the 2D imaging mode, and
wherein angles of individual X-rays outputted from the first and the second X-ray tubes and angles of the first and the second lower collimators are controlled such that the individual X-rays passing therethrough are transmitted toward the first and the second reflection units and at the same time angles of the first and the second reflection units and angles of the first and the second upper collimators are controlled such that the individual X-rays passing through the first and the second upper collimators are transmitted toward an area to be treated on the subject during the 3D imaging mode.

4. The fluoroscopic device of claim 1, wherein the detector is curved.

5. The fluoroscopic device of claim 1, wherein the image processing unit includes:
a first TV camera and a second TV camera for respectively taking the first X-ray and the second X-ray detected from the detector;
a TV projector for projecting images taken by the first and the second TV cameras;
an image controller for recombining and calibrating the images projected from the TV projector; and
a digital imaging unit for converting the recombined images into digital and analog signals; and
wherein the digital imaging unit is operable to provide the digital and analog signals to a monitor to be outputted as 2D or 3D images, wherein the 3D images are observable through 3D goggles.

6. The fluoroscopic device of claim 5, wherein the image controller calibrates the images projected from the TV projector during the 3D imaging mode by measuring distances between each of the images projected from the TV projector and the 3D goggles.

7. The fluoroscopic device of claim 5, wherein the image controller recombines and calibrates the image projected from the TV projector in consideration of an artifact by at least one of breath of the subject, movement of the subject, contrast, inversion of black and white, emphasis of specific frequencies by processing spatial filtering, improvement of a signal-to-noise ratio, concentration, and distance measuring.

8. The fluoroscopic device of claim 5, wherein the 3D goggles include a module for shielding the first and the second X-rays to prevent at least one eye of an observer from being damaged.

9. The fluoroscopic device of claim 1, comprising:
a C-arm, wherein the X-ray generator and the detector are mounted on the C-arm; and
a table, wherein the table is configured for placing the subject thereon.

* * * * *